| United States Patent [19] | [11] Patent Number: 5,009,891 |
|---|---|
| Niwa et al. | [45] Date of Patent: Apr. 23, 1991 |

[54] ANTIOXIDANT COMPOSITION OF NATURAL PRODUCTS AND PRODUCING METHOD THEREOF

[75] Inventors: Kozo Niwa, 4-4, Asahi-machi, Tosa-Shimizu, Kochi; Shimesu Motoyama, Asaka, both of Japan

[73] Assignee: Kozo Niwa, Kochi, Japan

[21] Appl. No.: 100,166

[22] Filed: Sep. 23, 1987

[30] Foreign Application Priority Data

Sep. 25, 1986 [JP] Japan .................. 61-224791

[51] Int. Cl.$^5$ .............................. A61K 35/78
[52] U.S. Cl. ..................... 424/195.100; 514/474; 426/18; 426/31; 426/61
[58] Field of Search ............ 424/195.1; 435/243, 435/918; 426/18, 31, 61; 514/474

[56] References Cited

U.S. PATENT DOCUMENTS 4,029,819 6/1977 Michelson .................. 426/61

FOREIGN PATENT DOCUMENTS 0146247 8/1983 Japan ................... 426/18

60-110269 6/1985 Japan .

OTHER PUBLICATIONS

Beuchat, "Fungal Fermentation of Peanut Press Cake", *Biological Abstracts*, Feb. 15, 1978, 20535.
Hawley, *The Condensed Chemical Dictionary*, p. 898 (1981).

*Primary Examiner*—John W. Rollins
*Attorney, Agent, or Firm*—Kane, Dalsimer, Sullivan, Kurucz, Levy, Eisele and Richard

[57] ABSTRACT

Natural products with antioxidant activity and production method of thereof, their composition being effective in scavenging reactive oxygen species in the human body. Said natural products are produced by brewing plant seeds, grain and/or germs thereof, containing low-molecular-weight reactive oxygen species-scavenging substances, with microorganisms added thereto, and by adding oil obtained from heated plant to the product. Vitamin C, vitamin C derivatives, or plants containing these substances may be further added to the products.

13 Claims, No Drawings

ANTIOXIDANT COMPOSITION OF NATURAL PRODUCTS AND PRODUCING METHOD THEREOF

BACKGROUND OF THE INVENTION

1. Field of the Invention

The present invention relates to antioxidant composition and production method thereof, the composition being remarkably efficative for preventing from and improving various diseases and for maintaining health and beauty.

2. Related Art Statement

Methods for effectively preventing and improving various diseases have recently been developed and put into practice, and the average life-span of humans has been prolonged accordingly. However, adult diseases such as arteriosclerosis, cerebral apoplexy, myocardial infarction, cancer, and diabetes; adult diseases such as malignant rheumarthritis, Behçet's disease, Crohn's disease, and ulcerative colitis; and diseases induced by chemical substances have attracted attention as major problems from the viewpoint of maintaining health.

Although such diseases do not occur by the same cause, it is known, as a mechanism of directly damaging the human body, that excessive reactive oxygen species or lipoperoxides (simply referred collectively to as "reactive oxygen species" hereinafter) are produced in the human body by various types of external irritations including public pollutants, and contribute to the damage of tissues, leading to the occurrences of diseases.

The human body contains enzyme called superoxide dismutase (SOD) which scavenges this excessive reactive oxygen and protects the tissues of the body from damage, so that the enzymes may act to maintain health by scavenging any excess of reactive oxygen species and thus prevent us from diseases.

However, it has recently been proven that adult diseases occur, particularly in those over 40, because the above-described SOD activity is gradually reduced with age, and that, if an excess of reactive oxygen species is produced by chronic or acute irritation by chemically produced products, the human body becomes short of SOD activity and thus suffers from diseases, such as those described above. Therefore, the preserving SOD levels has attracted attention in the medical field.

It is therefore attempted to improve diseases induced by an increase in reactive oxygen species or a decrease in SOD activity or prevent from diseases by uptake of SOD. The method currently available by which SOD is administered into the body is only the SOD injection, and liposome-encapsulated SOD injection is increasingly recognized in Japan and France that this method has remarkable effects in the treatment of inveterate diseases such as Behçet's disease, malignant rheumarthritis, Kawasaki disease, ulcerative colitis, and Crohn's disease; and adult diseases such as cerebral apoplexy, myocardial infarction, and diabetes; and in the prevention of cancer and aging.

However, of the various forms of SOD drugs, only the effect of injection drugs is scientifically and medically recognized, while the effect of oral medicines has not been proven yet. This is because SOD is denatured by gastric juices, and it cannot be absorbed by the alimentary canal as it is, owing to its high molecular weight of 30000 or more.

In addition, SOD has a demerit of limitation in that it acts on superoxide ($O_2^-$) alone of the four reactive oxygen species.

Although, as described above, only an injection drug is currently available and effective as a drug to be effective in above-described disease, it is obvious that oral medicines would be more convenient for both doctors and patients, and would be simple and desirable for, in particular, long-term use to cure or prevention from the disease or maintain health.

In addition, in order to take SOD products, not as a medical drug, but as a health food, it is assumed that SOD products should be orally administered, and it is expected that SOD products with remarkable reactive oxygen species scavenging effect should be developed. Japanese Patent Laid-Open No. 60-110269 discloses a botanical nutrient obtained by mixing sesame oil and/or soybean oil extracted from sesame and/or soybean with the heated rice bran, wheat, "hatomugi" (oriental barley), wheat germ soybean, and green tea, to which a small amount of "koji" fungus (*Aspergillus oryzae*) is added.

The above-described publication states that this botanical nutrient contains marked SOD-like activity and is effective for the above-described diseases.

However, even if this botanical nutrient contains SOD-like activity, the SOD has a disadvantage in that it cannot be absorbed through gastro-intestinal tract the alimentary canal, as stated above, and, even if it could be absorbed, SOD is only effective for superoxide of the reactive oxygen species, $H_2O_2$ being adversely increased.

It is experimentally recognized that raw, untreated product of the above-described material has lower reactive oxygen species scavenging action than treated material, and is so to speak, no more than a simple nutrient.

SUMMARY OF THE INVENTION

It an object of the present invention to provide antioxidant composition of our natural product production method thereof, the composition having a remarkable action in scavenging reactive oxygen species and marked effect on the treatment of or prevention from various disease caused by an excess of reactive oxygen species in the human body, being also effective for maintaining beauty and health.

The above-described and other objects, advantages, and novel characteristics of the present invention will become clear from reading the detailed description below and the accompanying claims.

An antioxidant composition of our natural products and prodution method thereof in accordance with the present invention are described in detail below.

The products with antioxidant activity according to the present invention is obtained by brewing the heated plant seeds, grain and/or the germs thereof with microorganisms added, and the addition of oil obtained from heated sesame and/or soybean.

The present invention also provides a composition with antioxidant activity which is produced by brewing heated plant seed, grain and/or the germs thereof with microorganisms added, and the addition of oil obtained from heated plants and vitamin C, vitamin C derivatives, or plants containing such substances.

Plant seeds and grain, particularly germs of soybean, sesame, "hatomugi" (a kind of oriental barley) and rice bran, generally contain low-molecular-weight substances with antioxidant activity such as flavonoids, polyphenols, tannin, tocopherol, carotene and vitamin $B_2$. However, since these substances form huge polymer of inactive substances in the forms of bonds or repeating subunits of polymers, binding to other components or each other, resulting in high-molecular-weight, the above-described plant seeds, grain or the germs thereof exhibit only a small antioxidant activity if taken as they are, and thus cannot be effective in the treatment of or prevention from diseases.

However, if these plant seeds, grain or their germs are treated with heating under continual stirring, and mild and appropriate temperature, substances with antioxidant activity are-liberated from the polymers to produce the original low-molecular-weight substances, and thereafter become free to be activated to show active antioxidant action, resulting in a marked increase in reactive oxygen species scavenging effect when compared with these untreated plant seeds, grain or germs thereof.

On the other hand, if the plant seeds, grain or germs thereof are heated with higher temperature, the substances with antioxidant activity contained therein are inactivated and the activity thereof is decreased.

It is therefore necessary to pay particular attention to the heating procedures, the heating temperature, or the heating time.

The term "heating" used in the present invention indicates that the heat required for activation is to heat materials without degrading the constitutive molecules, especially on the surface, and contribute to even transfer of heat to the center of materials. The heating temperature cannot be uniformly defined because it depends upon the kind of plant used and other heating conditions, but it is preferably from 50° to 150° C., and in many cases, 50° to 100° C.

It is necessary during the heating to uniformly heat the plant seeds, grain or germs thereof so that differences in temperature may be as small as possible between the internal and external layers of the particles thereof. For this purpose, methods of heating by far-infrared rays, continual heating by an incubator, or heating by a fluidized bed can be employed, but the heating method is not limited to any of these methods.

Examples of methods of heating is by far-infrared rays which is irradiated when materials are heated in a pottery vessel on an earthen or stony oven; sand, bricks, ceramics can be substituted for pottery, stone and earthenware.

Plant seeds and grain defined in the present invention include rice, wheat, barley, maize, hatomugi, adzuki bean, pea and sesame, and the plant seeds and grain defined are ,not limited to these described ones so long as they have strong effects of antioxidant activity.

Any one of the germs of the above-described plant seeds can be used as a germ, and among them rice bran and wheat germs are particularly preferable.

When plant seeds, grain and germs are used in mixture, the amount of the germs used is preferably 5 wt % or more of the total amount of the plant seeds, grain and the germs. And yet, 10% or more is most preferable.

After the heating, these plant seeds, grain or germs are brewed with microorganisms thereto.

It is generally required to brew them for about 2 to 3 days.

The term "to brew" used here indicates brewing in a wide sense, denoting that organic substances are decomposed by microorganisms, and does not indicate only the case in which the metabolites are converted to form a simple compound.

For example, brewing includes mild degradation using "koji" (*Aspergillus oryzae*) or yeast, and it is preferable to use them. In this brewing process, a larger amount of the above-described low-molecular-weight antioxidant substances is liberated by the action of an enzyme, such as the protease contained in "koji", so that their antioxidant activities are increased. Further, in addition to "koji" fungus and yeast, plants which contain microorganisms having brewing capacity such as a fig-rind, grape-rind, ripe pineapple or papaya may be used.

In the present invention, botanical oil obtained from heated plants is added after the heating and brewing processes.

The addition of the above botanical oil increases the quantity of substances with antioxidant activity, such as tocopherol, and further potentiates their actions.

Depending on circumstances, it is expected that portions soluble in botanical oil and portions insoluble therein could be separated from each other so that each separated portion can be used properly depending upon diseases.

Examples of materials for botanical oil include sesame seed, soybean, cotton seed, maize, safflower, evening primrose, rice bran, rapeseed, and olive, which are commonly used for foods or drugs, and the botanical materials used to extract the oil are not limited to these above described plants. Of these plants, sesame seed is preferable.

The present invention also provides a composition with antioxidant activity, by adding vitamin C, vitamin C derivatives, or plants containing these substances to the above-described materials produced by our procedures (heating+brewing+the addition of oil obtained from heated plant).

Vitamin C or derivatives thereof, which are substances with strong reducing activity, act to scavenge reactive oxygen species and prevent "koji" etc. from disintegration, so that the above-described composition is stabilized thereby and antioxidant actions of the free substances produced therefrom, such as tocopherol, polyphenols, flavonoids, tannin, and vitamin $B_2$, are further strengthened, resulting in a synergetic effect which enables a great increase in antioxidant activity.

Examples of vitamin C derivatives include salts sodium or potasisium salt of vitamin C and esters such as vitamin C palmitate.

Although various plants such as the immature green leaves and roots of barley and "daikon" (radish), fruits of lemon and "yuzu" (citron), green tea, and spinach can be used as plants containing vitamin C or derivatives thereof, it is a matter of course that the plants are not limited to these plants alone.

Such plants may be added as they are after being ground, as juices, or as powder of extract after being dried up, as long as they contain vitamin C or derivatives thereof. The respective ingredients may be added in any desired order.

If required, auxiliary drugs and ingredients which are health-promoting, such as various vitamins; chemical ingredients, such as metals or iodine which are necessary for a human body; or ingredients which are used for the preparation of corrigents, perfumes, tinctures, surfactants, excipients etc., may be appropriately added to the composition of our natural products in the present invention.

The composition of the present invention is preferably used not only as a drug for treating or preventing from adult diseases and adult diseases such as arteriosclerosis, cerebral apoplexy, myocardial infarction, diabetes, malignant rheumarthritis, Behçet's disease, Crohn's disease, ulcerative colitis, and Raynaud's disease; various disease caused by environmental pollution; spots; freckles; wart; ambustion; traumatic wounds; keloid; general malaise; hang over; and constipation; but also as a health food which is effective in maintaining beauty and health.

Since our natural products acted on all of the four reactive oxygen species, i.e., on $O_2^-$, $H_2O_2$, .OH and $^1O_2$, they are considered to have an advantage in that its effect is greater than that of SOD (superoxide dismutase).

In addition, since the above-described antioxidant activity in the products was stable and increased in the presence of stomach acids, and since the products were decomposed by the stomach acids to produce low-molecular-weight compounds, resulting in showing a marked effect in antioxidant activity (refer to *Inflammation*, Vol. 10, No. 1, 1986, by Niwa, et al.), the products can be used for the treatment, prevention, and maintenance of health by oral administration.

It is also possible to use the products topically for the treatment of burn, wounds of general trauma, or dermatoses.

DESCRIPTION OF THE PREFERRED EMBODIMENTS

A description is made below of the efficacy in antioxidant activity of the sample which consist of various combinations with various materials for our products, but the present invention is not limited to these examples.

Each sample was prepared in accordance with the following methods:

Sample 1A 100 g of rice bran was put in a ceramic-coated vessel and gradually heated at about 70° C. in such a way that it was not over heated, then it was ground. 20 mg of commercially-available "koji" was added to the ground rice bran, and the mixture was then brewed (malted) for 72 hours at 33° C.

Sample 1B

The same procedure as that of Sample 1A was performed, with the exception that wheat germ was used in place of the rice bran.

Sample 1C

The same procedure as that of Sample 1A was performed, with the exception that wheat was used in place of the rice bran.

Sample 1D 100 g of soybeans were put in an iron vessel and gradually heated under stirring together with 500 g of sand at about 80° C. in such a way that they were not over heated. The soybeans were separated from the sand by the difference of gravity between soybeans and sand, and then ground. 30 mg of commercially-available "koji" was added to the ground soybeans, and the mixture was then brewed for 72 hours at 32° C.

Sample 1E

The same procedure as that of Sample 1A was performed, with the exception that "hatomugi" (a kind of barley) was used in place of the rice bran.

Sample 1F

Sesame seeds were put in a thick earthenware vessel, were heated at about 80° C. in such a way that they were not over heated, and then were ground.

Sample 2A

Sample 1F was crushed to extract oil therefrom.

Sample 2B

The same procedure as that of Sample 2A was performed, with the exception that heated soybeans were used in place of the sesame seeds.

Sample 3A

Powdered green tea

Sample 3B

Juice pressed from "yuzu" (citron)

Sample 3C

Powder extracted by drying up the immature leaves of barley at a low temperature

Sample 3D

Synthetic (chemically produced) vitamin C

EXAMPLES AND EFFECTS

The efficacy in antioxidant activity of the thus-obtained samples of various combination materials are shown in Table 1 comparing them with the control samples.

TABLE 1

| Classification | No. | Composition of each sample | Active oxygen-inhibiting effect | | | |
|---|---|---|---|---|---|---|
| | | | $O_2^-$ | $H_2O_2$ | .OH | $^1O_2$ |
| Test Example | 1 | 1A:2A = 90:10 (weight ratio) | 28 | 24 | 23 | 25 |
| | 2 | 1A:2B = 90:10 | 26 | 22 | 22 | 21 |
| | 3 | 1B:2A = 90:10 | 30 | 28 | 25 | 27 |
| | 4 | 1A:2A:3A = 80:10:10 | 46 | 48 | 41 | 44 |
| | 5 | 1A:1C:2A:3B = 15:65:10:10 | 51 | 50 | 47 | 50 |
| | 6 | 1A:1C:2A:3B = 40:40:10:10 | 60 | 62 | 61 | 63 |
| | 7 | 1A:1B:1C:1D:1E:1F: 2A:3A = 13:13:13:13: 13:7:12:16 | 75 | 72 | 77 | 75 |
| | 8 | 2B was used in place of 2A of No. 7 | 68 | 65 | 66 | 67 |
| | 9 | 10 parts of 3B were added to 100 parts of No. 7 | 85 | 80 | 88 | 87 |
| | 10 | 3C was used in place of 3A of No. 7 | 77 | 75 | 72 | 74 |
| | 11 | 3D was used in place of 3A of No. 7 | 70 | 67 | 68 | 67 |
| Control Examples | 1 | Same sample as No. 1, but not subjected to heating and fermentation | 6 | 5 | 6 | 4 |
| | 2 | Same sample as No. 7, but not subjected to heating and fermentation | 8 | 8 | 6 | 6 |
| | 3 | Same sample as No. 7, but heated with- | 3 | 2 | 4 | 2 |

TABLE 1-continued

| Classification | No. | Composition of each sample | Active oxygen-inhibiting effect | | | |
|---|---|---|---|---|---|---|
| | | | $O_2^-$ | $H_2O_2$ | .OH | $^1O_2$ |
| | | out far-infrared rays and having over heated surfaces | | | | |
| | 4 | Same sample as No. 7, but containing oil obtained from non-heated sesame seeds different from 2A | 7 | 8 | 7 | 9 |

Note
(1): The numerical values of active oxygen-inhibiting effects are % ratios of reductions in active oxygen levels generated in test tubes, measured by the method described below.
(2): The values for $^1O_2$ were obtained by measurements of chemiluminescence.

The results of clinical tests performed with respect to Examples 1, 4, 7, and 9 and control Examples 2 and 4 of Table 1 are shown in Table 2.

TABLE 2

| | | Disease | | | |
|---|---|---|---|---|---|
| | | Rhematoid arthritis | Raynaud's disease | ephlides, freckles | hang over |
| | | Dosage per day | | | |
| | | 15 g | 9 g | 9 g | 12 g |
| | | Administration period | | | |
| | | 3 months | 1 months | 4 months | Once (after over drink) |
| Test examples | 1 | 2/6 | 2/6 | 1/6 | 3/6 |
| | 4 | 3/6 | 2/5 | 1/6 | 3/6 |
| | 7 | 11/18 | 4/6 | 6/18 | 13/20 |
| | 9 | 16/22 | 6/8 | 6/15 | 14/20 |
| Control Examples | 2 | 0/8 | 0/5 | 0/6 | 0/4 |
| | 4 | 0/8 | 0/6 | 0/4 | 1/5 |

Note
The numerical values in the table indicate the ratios of the number of the patients with effective results to that of the cases tested.

The assessment of antioxidant effects of the samples shown in Table 1 were performed according to the method described by Niwa, et al. (*Inflammation* Vol. 10, No. 1, 1986, pp. 80-81). The method is briefly described below.

Each of the test samples of the present invention was subjected to be sonified, and then was added to an reactive oxygen species-generating system (human peripheral blood neutrophils and xanthine-xanthine oxidase); the therapeutic dose (in terms of its expected serum concentration after administration in the human body) of each sample (1.6 mg/ml) was added. Reactive oxygen species levels generated in the presence of each test sample were measured and were compared with those obtained from control samples to which no composition of the present invention was correlated.

The above-described therapeutic dose is the expected serum concentration of the composition of the present invention, when a generally-used dose per day (10 g of the composition of the present invention) is absorbed by the body.

The four reactive oxygen species were measured according to the following method:

For $O_2^-$, the amount of reduction of ferricytochrome c by $O_2^-$ was measured by a Beckman spectrophotometer at an absorbance of 550 nm, then this was converted into the amount of $O_2^-$. For $H_2O_2$, since $H_2O_2$ reduces the fluorescence emitted by scopoletin in the presence of peroxidase, the reduction in the fluorescence emitted by scopoletin was measured using scopoletin and peroxidase by a fluorescent spectrophotometer produced by Hitachi Ltd. at an excitation wavelength of 370 nm and an emission wavelength of 460 nm.

For .OH, on the basis of the principle that .OH reacts with α-keto-methiol butylic acid (KMB) to produce ethylene ($C_2H_4$), the quantity of ethylene gas was determined by gas chromatography of Hitachi Ltd. and was converted into the amount of .OH.

The chemiluminescence ($^1O_2$) was measured by using a liquid scintillation counter under conditions in which no luminol was added and no light was permitted.

What is claimed is:

1. An antioxidant composition, which comprises; the product obtained by steps consisting of
   (a) heating a material selected from the group consisting of plant seeds, vegetable grains and germs thereof, or rice bran to a temperature within the range of from 50° to 150° C. for a period of time sufficient to release low-molecular weight antioxidant compounds from bonds or repeating sub-units of polymers binding the compounds to other components or each other;
   (b) brewing the heated material; and
   (c) adding to the brew, an oil, obtained from a plant heated to a temperature within the range of from 50° to 150° C. for a period of time sufficient to release low-molecular weight antioxidant compounds from bonds or repeating sub-units of polymers binding the compounds to other components or each other.

2. A composition of claim 1 wherein the material selected is a mixture of plant seeds, vegetable grains and at least 5% by weight of germs.

3. A composition of claim 1 wherein the material selected comprises rice bran or wheat germ.

4. A composition of claim 1 wherein the botanical oil is sesame oil.

5. A composition of claim 1 to which vitamin C, vitamin C derivatives or plants containing such a substance has been added.

6. A composition of claim 5 wherein the material selected is a mixture of plant seeds, grain and at least 5% by weight of germs.

7. A composition of claim 5 wherein the material selected comprises rice bran or wheat germ.

8. A composition of claim 5 wherein the oil is sesame oil.

9. A method of preparing an antioxidant composition, which comprises;
   (a) heating a material selected from the group consisting of plant seeds, vegetable grains and germs thereof or rice bran to a temperature of from 50° to 150° C. for a period of time sufficient to release low-molecular weight antioxidant compounds from bonds or repeating sub-units of polymers bonding the compounds to other components or each other;
   (b) brewing the heated material; and
   (c) adding to the brew an oil obtained from a plant heated to a temperature within the range of from =° to 150° C. for a period of time sufficient to release low-molecular weight antioxidant compounds from bonds or repeating sub-units of polymers binding the compounds to other components or each other.

10. The method of claim 9 wherein heating is carried out in a vessel made of a ceramic-coated metal or pottery earthen material.

11. The method of claim 9 wherein heating is carried out by far-infrared radiation.

12. The method of claim 9 wherein brewing is carried out in the presence of Koji fungus.

13. A method of claim 9 further comprises adding vitamin C, vitamin C derivatives or plants containing such a substance to the final mixture.

* * * * *